United States Patent [19]

Kowaleski

[11] Patent Number: 5,801,259
[45] Date of Patent: Sep. 1, 1998

[54] ETHYLENE OXIDE CATALYST AND PROCESS

[75] Inventor: Ruth Mary Kowaleski, Houston, Tex.

[73] Assignee: Shell Oil Company, Houston, Tex.

[21] Appl. No.: 643,158

[22] Filed: Apr. 30, 1996

[51] Int. Cl.⁶ .......................................... C07D 301/03
[52] U.S. Cl. ........................ 549/536; 502/348; 549/537
[58] Field of Search ............................ 549/536, 537; 502/348

[56] References Cited

U.S. PATENT DOCUMENTS

| | | | |
|---|---|---|---|
| 3,172,866 | 3/1965 | Belon | 502/439 |
| 3,316,279 | 4/1967 | Fenton | 260/348.5 |
| 3,702,259 | 11/1972 | Nielsen | 117/37 R |
| 3,844,981 | 10/1974 | Cusumano | 252/471 |
| 3,962,136 | 6/1976 | Nielsen et al. | 252/454 |
| 3,962,285 | 6/1976 | Cusumano | 260/348.5 R |
| 3,972,829 | 8/1976 | Michalko | 252/430 |
| 4,005,049 | 1/1977 | Fields | 252/467 |
| 4,010,115 | 3/1977 | Nielsen et al. | 252/454 |
| 4,012,425 | 3/1977 | Nielsen et al. | 260/348.5 R |
| 4,212,772 | 7/1980 | Mross et al. | 252/476 |
| 4,272,443 | 6/1981 | Titzenthaler et al. | 260/348.34 |
| 4,278,562 | 7/1981 | Mross et al. | 252/430 |
| 4,324,699 | 4/1982 | Mross et al. | 252/463 |
| 4,356,312 | 10/1982 | Nielsen et al. | 549/534 |
| 4,428,863 | 1/1984 | Fry | 502/8 |
| 4,444,899 | 4/1984 | Yamada et al. | 502/355 |
| 4,459,372 | 7/1984 | Arena | 502/351 |
| 4,532,231 | 7/1985 | Johnson | 502/347 |
| 4,536,482 | 8/1985 | Carcia | 502/177 |
| 4,548,921 | 10/1985 | Gues et al. | 502/330 |
| 4,621,071 | 11/1986 | Blanchard | 502/302 |
| 4,711,873 | 12/1987 | Suzukamo et al. | 502/344 |
| 4,742,034 | 5/1988 | Boxhoorn et al. | 502/231 |
| 4,761,394 | 8/1988 | Lauritzen | 502/348 |
| 4,766,105 | 8/1988 | Lauritzen | 502/216 |
| 4,786,626 | 11/1988 | Suzukamo et al. | 502/344 |
| 4,808,738 | 2/1989 | Lauritzen | 549/536 |
| 4,837,194 | 6/1989 | Hayden | 502/348 |
| 4,874,739 | 10/1989 | Boxhoorn | 502/218 |
| 4,897,498 | 1/1990 | Monnier et al. | 549/534 |
| 4,908,343 | 3/1990 | Bhasin | 502/218 |
| 4,992,409 | 2/1991 | Michaels et al. | 502/341 |
| 5,011,809 | 4/1991 | Herzog | 502/348 |
| 5,028,577 | 7/1991 | Michaels et al. | 502/243 |
| 5,037,794 | 8/1991 | Magistro | 502/355 |
| 5,055,442 | 10/1991 | Osaka et al. | 502/439 |
| 5,057,481 | 10/1991 | Bhasin | 502/208 |
| 5,063,195 | 11/1991 | Jin et al. | 502/348 |
| 5,071,815 | 12/1991 | Wallace et al. | 502/302 |
| 5,072,886 | 12/1991 | Morrison et al. | 241/1 |
| 5,081,096 | 1/1992 | Monnier et al. | 502/348 |
| 5,081,324 | 1/1992 | Michaels et al. | 585/500 |
| 5,100,859 | 3/1992 | Gerdes et al. | 502/439 |
| 5,102,848 | 4/1992 | Soo et al. | 502/218 |
| 5,130,286 | 7/1992 | Michaels et al. | 502/341 |
| 5,153,165 | 10/1992 | Lowery et al. | 502/341 |
| 5,380,697 | 1/1995 | Matusz et al. | 502/348 |
| 5,384,302 | 1/1995 | Gerdes et al. | 502/439 |
| 5,395,812 | 3/1995 | Nagase et al. | 502/238 |

FOREIGN PATENT DOCUMENTS

| | | |
|---|---|---|
| 199396 | 10/1986 | European Pat. Off. . |
| 327356 | 6/1989 | European Pat. Off. . |
| 501317 | 3/1991 | European Pat. Off. . |
| 56108533 | 1/1980 | Japan . |
| 4363139-A | 6/1991 | Japan . |
| 1325715 | 8/1973 | United Kingdom . |
| 96/23585 | 8/1996 | WIPO . |

OTHER PUBLICATIONS

Patent search Report of Jul. 17, 1997.

*Primary Examiner*—C. Warren Ivy
*Assistant Examiner*—Garth M. Dahlen
*Attorney, Agent, or Firm*—Pamela J. McCollough

[57] ABSTRACT

This invention relates to an ethylene oxide catalyst which contains silver and one or more alkali metal promoters supported on a carrier prepared by a process comprising the use of ceramic particle components with particle sizes chosen to ensure that a desired degree of porosity is obtained without the use of organic burnout materials.

26 Claims, No Drawings

ETHYLENE OXIDE CATALYST AND PROCESS

FIELD OF THE INVENTION

The invention relates to silver-containing catalysts suitable for the preparation of ethylene oxide and to the use of the catalysts for the preparation of ethylene oxide. The catalysts are prepared using a unique alpha alumina-based catalyst carrier.

BACKGROUND OF THE INVENTION

Catalysts for the production of ethylene oxide from ethylene and molecular oxygen are generally supported silver catalysts. Such catalysts are typically promoted with alkali metals. The use of small amounts of the alkali metals potassium, rubidium and cesium were noted as useful promoters in supported silver catalysts in U.S. Pat. No. 3,962,136, issued Jun. 8, 1976, and U.S. Pat. No. 4,010,115, issued Mar. 1, 1977. The use of other co-promoters, such as rhenium, or rhenium along with sulfur, molybdenum, tungsten and chromium is disclosed in U.S. Pat. No. 4,766,105, issued Aug. 23, 1988, and U.S. Pat. No. 4,808,738, issued Feb. 28, 1989. U.S. Pat. No. 4,908,343, issued Mar. 13, 1990, discloses a supported silver catalyst containing a mixture of a cesium salt and one or more alkali metal and alkaline earth metal salts.

The use of porous ceramic catalyst carriers has been previously described in a number of patents such as, for example, U.S. Pat. No. 5,380,697, issued Jan. 10, 1995, U.S. Pat. No. 5,100,859, issued Mar. 31, 1992, U.S. Pat. No. 5,055,442, issued Oct. 8, 1991, U.S. Pat. No. 5,037,794, issued Aug. 6, 1991, and U.S. Pat. No. 4,874,739, issued Oct. 17, 1989. Such catalyst carriers have a wide variety of potential applications in the catalytic field and are especially useful where the ceramic base is an alumina such as alpha alumina.

A catalyst support needs to possess, in combination, at least a minimum surface area on which the catalytic component may be deposited, high water absorption and crush strength. The problem is that usually an increase in one can mean a reduction in another property. Thus, high crush strength may mean low porosity. Often the balance is achieved by trial and error making the catalyst carrier art even more unpredictable than other chemical process art.

Carriers need to have a uniform degree of porosity and this may be achieved in a number of ways including the incorporation of burnout materials that are eliminated when the ceramic is fired to form the finished product. Typical burnout materials include charcoal, petroleum coke, ground walnut shells and the like. The problem is that such materials usually leave leachable residues that can significantly impair the performance of catalysts supported on carriers made using such burnout materials. Furthermore, the actual content of such leachable material varies widely from batch to batch so that predictability is unsatisfactory. In an attempt to circumvent this problem, it has been proposed to incorporate organic polymeric burnout materials with very low metallic leachables content (U.S. Ser. No. 08/383,020, filed Feb. 1, 1995). However, such burnout materials still leave result-affecting traces of residue.

There is therefore a need to design catalysts in which one can have confidence with respect to the final property balance. The catalysts of the present invention have an excellent balance of crush strength, abrasion resistance, porosity and catalytic performance that make them ideal for a wide range of catalytic applications. More importantly, the amount of metallic leachables has been significantly reduced without parallel negative effects on the physical properties of the catalyst. The present invention therefore results in catalysts which have improved selectivity and/or activity stability.

SUMMARY OF THE INVENTION

This invention relates to a catalyst suitable for the production of ethylene oxide from ethylene and molecular oxygen in the vapor phase which catalyst comprises a catalytically effective amount of silver and a promoting amount of alkali metal supported on a catalyst carrier prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier.

It has been found that catalysts supported on these carriers have improved selectivity and/or activity stability.

DESCRIPTION OF THE PREFERRED EMBODIMENTS

The catalysts of the present invention comprise a catalytically effective amount of silver and a promoting amount of alkali metal supported on an alpha alumina-based catalyst carrier produced by a novel production method which does not require the presence of pore-inducing burnout materials. Descriptions of the carrier, the catalyst prepared with the carrier and the use of the catalyst are provided in detail below.

The Carrier

The ceramic catalyst carrier of the present invention is prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier.

The invention further provides a catalyst supported on a carrier prepared by a novel process for the production of an alpha alumina-based catalyst carrier which does not require the presence of pore-inducing burnout materials. The process provides a carrier that has no metallic oxide leachables present as a result of the burnout of the pore formers. Some leachables, and particularly some metallic leachables, are known to adversely affect the stability of the selectivity and/or the activity of a catalyst deposited on the carrier in that, using prior art catalysts on carriers with conventional amounts of metallic leachables, these parameters decline over time. Since the amount of leachables in organic burnout materials is subject to considerable variability, the impact on the performance from batch to batch likewise varies. Thus, predictability in performance is significantly and adversely impacted by the leachables. Leachables may arise from several sources but by eliminating one very significant source, the organic burnout material, the variability of performance impact is reduced. Moreover, while with the carriers of the present invention there is still a decline in selectivity over time, the rate of such decline is greatly reduced making the catalysts prepared using such carriers able to perform at acceptable levels for significantly longer periods.

The term "metallic leachables", as used in this specification, refers to the total amount of the elements sodium, potassium, calcium and aluminum present in the carrier measured in parts by weight per million. It is calculated by boiling a standard amount of the finished carrier in a standard volume of 10% nitric acid for 30 minutes. This extracts the metals in the form of the soluble nitrates which may then be analyzed for the residual metallic values.

The catalyst carrier is prepared by a process which comprises providing a mixture of ceramic components comprising at least 80 percent by weight by weight of alpha alumina particles, 0.01 percent by weight to about 10 percent by weight by weight of an alkaline earth metal oxide selected from calcium and magnesium oxides, 0.01 percent by weight to about 10 percent by weight, (measured as silica), of a silicon oxide and from zero to about 15 percent by weight by weight, measured as the dioxide) of zirconia, (all proportions being measured on the basis of the weight of the finished carrier), a liquid carrier medium and optionally a ceramic bond, a lubricant and/or extrusion aids; shaping the mixture to form a carrier precursor; drying the carrier precursor to remove the liquid carrier medium; and then firing the precursor to form an alpha alumina carrier with a porosity that is preferably from about 15 percent to about 60 percent, wherein the sizes of the alpha alumina particles are chosen such that the porosity of the dried precursor, after making allowance for the presence of the lubricant and extrusion aids, is not less than the porosity of the fired carrier.

The above process introduces porosity in the form of the natural porosity that results when large particles are sintered together, modified by the presence of smaller particles that fill up some of the spaces between the larger particles until exactly the desired degree of porosity is achieved. This is in contrast to the prior art approach of forming porosity by inclusion of material subsequently burned out. As a result of the absence of the conventional burnout material, the process of the invention can also be characterized in that the loss of weight upon firing the dried extrudate is less than about 15 percent, which is the maximum amount of residual liquid carrier medium, (with water this is usually about 2 percent by weight), lubricants and extrusion aids that might conventionally be used to produce such carriers.

Because there are essentially no burnout pore formers present, (though some small amounts, for example up to about 5 percent of the weight of the ceramic components, may be added to assist in pore forming without departing from the essence of the invention), the dried precursor of the carrier usually has a porosity that is at least about 95 percent of that of the finished carrier, after making allowance for the presence of lubricants and extrusion aids. Some slight reduction of the porosity will be expected to occur upon firing as a result of the sintering together of the ceramic particles. There will, however, be no significant increase in porosity such as results when a burnout material is volatilized from the precursor.

Another indicator of the products made by the process of the invention is that the packing density, (measured by ASTM 4699-87, modified by the use of a cylinder with an inside diameter of 33 ¾ inches and a length of 18 inches, or the equivalent), is frequently less than about 10 percent greater for the green, unfired carrier than for the fired carrier. Indeed, typically the density of the fired carrier is, if anything, slightly higher than that of the unfired carrier. A typical carrier made with organic burnout materials conventionally comprises about 20 percent by weight to about 35 percent by weight, based on the weight of the ceramic components, of material that is removed during firing and, of this amount from about 50 percent to about 75 percent is provided by the burnout materials. Thus the green packing density is typically from about 8 percent to 15 percent greater than the density of the corresponding fired carrier materials for conventionally formed carriers. By contrast, the difference in green packing density and fired density for the products of the invention is very small and usually the green pack density is up to about 2 percent greater than the unfired density. After making allowance for the presence of lubricants and extrusion aids in the unfired material, the density difference is insignificant.

Manipulation of the porosity can be achieved according to the invention in a number of ways. For example, it is possible to use relatively large particles of a first alumina component such as particles from about 15 microns to about 120 microns in average particle size and then add relatively small alumina particles with average particle sizes of from about 1 micron to about 15 microns. The proportions in which the components appear is dictated by the final desired porosity and the desired average pore size.

When a bimodal particle size distribution is chosen, the larger particle size component can be supplied by monolithic particles or alternatively, and sometimes preferably, they may be supplied in the form of lightly sintered alpha alumina agglomerates. This is often the form of commercial alpha alumina components which can relatively easily be comminuted to a uniform fine particle size by a conventional milling operation. The intensity of the milling required will depend largely on the degree of sintering that accompanied the conversion to the alpha phase. By initiating the process with agglomerated alumina components and then subjecting the agglomerates to a milling operation sufficient to generate exactly the correct amount of the finer particles, a blend of particle sizes can be generated with exactly the desired porosity in the final carrier. With lightly sintered alumina agglomerates, this milling operation can be supplied by the normal mixing and extruding operations involved in producing the carrier material and this is often a preferred way of operating especially where the unmilled agglomerated product has properties that are reasonably consistent from batch to batch. Therefore in a preferred manner of operating the alumina is provided in the form of unmilled agglomerated particles having a median agglomerated particle size of from about 15 microns to about 120 microns, more preferably from about 30 microns to about 90 microns, and most preferably from about 40 microns to about 80 microns, with the particles formed upon comminution having median particle sizes of from about 1 micron to about 6 microns, and preferably from about 1.5 microns to about 4 microns.

It is often preferred to use mixtures of ground alumina agglomerates with known particle size distribution and unground alpha alumina agglomerates and to ensure that the production process includes no operations that could result in unacceptable reduction in the average particle size of the agglomerate components.

The particles can have any desired configuration but since the objective is to produce a carrier material with a high but uniform porosity, this is most efficiently achieved if the larger particles have a generally blocky, i.e., more nearly spherical, configuration. In the same way, the smaller particles are also preferably somewhat blocky in shape.

The material from which the carrier is made is based predominantly on alpha alumina, with at least 80 percent and preferably 85 percent or even 90 percent or more of the weight of the finished carrier being provided by alpha alumina. However minor amounts of other ceramic oxides such as zirconia, titania, silica and/or alkaline earth metal oxides, (calcia, magnesia and strontia), may be present. The alpha alumina is present in the calcined carrier in an amount greater than about 80 percent by weight, preferably about 85 percent by weight, and more preferably about 95 percent by weight of the total carrier.

The calcium or magnesium oxide component of the carrier composition of the invention this can be present in an amount that represents from 0.01 percent by weight to about 10 percent by weight (measured as the oxide, MO,) of the carrier weight, but preferably the amount present is from about 0.03 percent by weight to about 5.0 percent by weight and especially from about 0.05 percent by weight to about 2.0 percent by weight.

The calcium and magnesium compounds that may be used to prepare the carriers for the catalyst of the present invention are oxides or compounds that are decomposable to or which form oxides upon calcination. Examples include carbonates, nitrates, and carboxylates. Other suitable compounds include the oxides themselves, and mixed oxides such as the aluminates, silicates, aluminosilicates, zirconates and the like. The preferred compounds are calcium silicate and magnesium silicate.

The silicon compounds used to prepare the carriers for the catalyst of the present invention are oxides or compounds decomposable to the oxides upon calcination. Suitable compounds include silicon dioxide itself, as well as the mixed oxides such as the alkaline earth metal silicates, zirconium silicates, aluminosilicates such as zeolites, hydrolyzable silicon compounds, polysiloxanes and the like. The amount used should be such as to provide, in the final carrier composition, from about 0.01 percent by weight to about 15.0 percent by weight, such as from about 0.03 percent by weight to about 10.0 percent by weight and most conveniently from about 0.05 percent by weight to about 5.0 percent by weight, (measured as silica).

The zirconia component, while optional, is preferably present in an amount that is from about 0.01 percent by weight to about 10.0 percent by weight, such as from about 0.3 percent by weight to about 5.0 percent by weight and especially from about 0.05 percent by weight to about 2.0 percent by weight based on the carrier weight. Where the zirconia is generated in situ, the amount used should be selected to give a final proportion within these parameters.

The zirconium compounds which may be used to prepare the carriers are oxides or compounds which are decomposable to or which form oxides upon calcination. Examples include carbonates, nitrates and carboxylates. Suitable compounds include zirconium nitrate, zirconium dioxide, as well as the mixed oxides such as zirconium silicates, zirconium aluminosilicates, zirconates and the like. The preferred compound is zirconium dioxide.

The alpha alumina component is most preferably combined with calcium silicate itself but, as indicated above, it is also possible to use a calcium oxide-generating compound and silica or a silica-generating compound in such proportions that on heating calcium silicate is produced. These components are mixed with zirconia or a zirconia-generating compound, (where present), a ceramic bond material, lubricants and/or extrusion aids and water, formed into shapes and calcined.

The formulation from which the carriers of the present catalyst is formed can also comprise a "binding agent" and this term, as used herein, refers to an agent that holds together the various components of the carrier prior to calcination to form an extrudable paste, i.e, the so-called low temperature binding agent. The binding agent also facilitates the extrusion process by adding lubricity. Typical binding agents include alumina gels, particularly in combination with a peptizing agent such as nitric or acetic acid. Also suitable are the carbon based materials, including celluloses and substituted celluloses such as methylcellulose, ethylcellulose and carboxyethylcellulose, stearates such as organic stearate esters, e.g. methyl or ethyl stearate, waxes, polyolefin oxides and the like. Preferred binding agents are petroleum jelly and polyolefin oxides.

The use of calcium or magnesium silicate, whether prepared directly or formed in situ with the constraints described above, can completely replace the need for a ceramic bond component. Even where it is considered necessary to use a ceramic bond component it is often possible to use ceramic bonds containing, overall, a lower amount of silica then is present in conventional bonds. It also permits the avoidance of an excess of silicon dioxide which typically contains deleterious amounts of sodium, iron and/or potassium impurities, especially when present in clays, bentonite and the like. As is known, the avoidance of such metallic impurities is a highly desirable objective.

The role of the zirconia, where used, is not fully understood but it appears to stabilize certain partial oxidation catalyst recipes. Calcium silicate appears to stabilize at least a proportion of the zirconia in the more active tetragonal form instead of the monoclinic form to which the mixed phase reverts when heated in the absence of calcium silicate.

The carrier and catalyst prepared therefrom may comprise a number of other ceramic-forming components chosen to contribute to the desired physical properties, including crush strength and the like. For example, components such as titania in amounts of up to about 5 percent by weight, are often found to confer particular advantage on such carrier materials. The titania can be added as a component of the initial mixture or it can be added to the porous calcined carrier by impregnation using a titanium salt that, for purposes of this specification, is presumed to decompose to the oxide during the firing operation.

After the components of the carrier are mixed together, for example by milling, the mixed material is formed, for example by extruding or pressing, into shaped pellets, for example, cylinders, rings, trilobes, tetralobes and the like. The formed material is dried to remove water that would convert to steam during calcination and destroy the physical integrity of the shapes. The drying and calcination can be combined in one step by suitable programming of the time and temperature. Calcining is carried out under conditions sufficient to volatilize lubricants, extrusion aids and binding agents and to fuse the alpha alumina particles into a porous, hard mass.

Calcination is typically carried out in an oxidizing atmosphere, such as oxygen gas or more preferably air and at a maximum temperature over 1300° C. and preferably ranging from about 1350° C. to about 1500° C. Times at these maximum temperatures can range from about 0.5 minutes to about 200 minutes.

The calcined carriers and catalysts prepared therefrom typically have pore volumes (water) ranging from about 0.2 cc/g to about 0.6 cc/g, and more preferably from about 0.3 cc/g to about 0.5 cc/g, and surface areas ranging from about 0.15 $m^2/g$ to about 3.0 $m^2/g$, and preferably from about 0.3 $m^2/g$ to about 2.0 $m^2/g$.

As indicated above, it may be necessary to add a ceramic bond material to the mixture to give added strength to the fired carrier. Conventional ceramic bond materials can be used in amounts of from about 0.2 percent by weight to about 5 percent by weight, based on the weight of the ceramic components in the composition, and after firing these typically comprise components, (expressed as the oxides), such as silica, alumina, aluminosilicates, alkaline earth metal oxides, alkali metal oxides and minor trace amounts of iron oxide and titanium oxide, with the first two being the dominant components.

The preferred porous alpha alumina based carriers for use in the catalyst of the instant invention have a metallic leachables content below about 2000 ppm and more preferably below about 1000 ppm. By comparison with carriers having similar porosities and packing densities made using the same ceramic components and with conventional burn-out materials, these carriers display a significantly greater selectivity stability in the oxidation of ethylene to ethylene oxide.

The carriers described above are particularly suited for preparing ethylene oxide catalysts which have improved selectivity and/or activity stability.

The Catalyst

The catalysts of the present invention comprise a catalytically effective amount of silver and a promoting amount of alkali metal(s) deposited on a carrier prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier. Other promoters in promoting amounts may be optionally present on the catalysts such as rare earths, magnesium, rhenium and rhenium co-promoters selected from sulfur, chromium, molybdenum, tungsten, phosphorus, boron and mixtures thereof.

In general, the catalysts of the present invention are prepared by impregnating porous refractory supports comprising alpha alumina with silver ions or compound(s), complex(es) and/or salt(s) dissolved in a suitable solvent sufficient to cause deposition on the support of from about 1 to about 40, preferably from about 1 to about 30 percent by weight, basis the weight of the total catalyst, of silver. The impregnated support is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier coincidentally with the deposition of the silver and/or alkali metal will be suitable optional promoter compound(s), complex(es) and/or salt(s) dissolved in an appropriate solvent.

The catalysts of the present invention are prepared by a technique in which the alkali metal promoter as well as any additional promoters in the form of soluble salts and/or compounds are deposited on the catalyst and/or support prior to, simultaneously with, or subsequent to the deposition of the silver, alkali metal, and any other promoters. The preferred method is to deposit silver, alkali metal and any other promoters simultaneously on the support, that is, in a single impregnation step, although it is believed that the individual or concurrent deposition of the alkali metal prior to and/or subsequent to the deposition of the silver would also produce suitable catalysts.

Promoting amounts of alkali metal or mixtures of alkali metal are deposited on a porous support using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, the silver content of the catalyst and the particular ions used in conjunction with the alkali metal cation, optional co-promoters. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions, and the above-defined limits were selected to cover the widest possible variations in properties and characteristics. The effects of these variation in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50% wt.) of the alkali metals are selected from the group consisting of potassium, rubidium, cesium, and mixtures thereof. As used herein, the term "alkali metal" and cognates thereof refers to the alkali metals selected from the group consisting of lithium, sodium, potassium, rubidium, cesium and mixtures thereof. As used herein, the term "mixtures of alkali metals" or cognates of these terms refers to the use of two or more of the alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium. A particularly preferred alkali metal promoter is cesium plus at least one additional alkali metal. The additional alkali metal is preferably selected from sodium, lithium and mixtures thereof, with lithium being preferred.

It should be understood that the amounts of alkali metal promoters on the catalysts are not necessarily the total amounts of these metals present in the catalyst. Rather, they are the amounts of alkali metal promoters which have been added to the catalyst by impregnation with a suitable solution of ions, salts and/or compounds and/or complexes of alkali metals. These amounts do not include amounts of alkali metals which are locked into the support, for example, by calcining, or are not extractable in a suitable solvent such as water or lower alkanol or amine or mixtures thereof and do not provide a promoting effect. It is also understood that a source of the alkali metal promoter ions, salts and/or compounds used to promote the catalyst may be the carrier. That is, the carrier may contain extractable amounts of alkali metal that can be extracted with a suitable solvent, such as water or lower alkanol. Thus, a catalyst prepared using such a carrier and an impregnating solution containing water or lower alkanol will have the alkali metal ions, salts and/or compounds deposited or redeposited on the catalyst.

Non-limiting examples of other promoters include rhenium, sulfate, molybdate, tungstate and chromate (see U.S. Pat. No. 4,766,105, issued Aug. 23, 1988), as well as phosphate and borate; sulfate anion, fluoride anion, oxyanions of Groups 3b to 6b (see U.S. Pat. No. 5,102,848, issued Apr. 7, 1992); (i) oxyanions of an element selected from Groups 3 through 7b and (ii) alkali(ne) metal salts with anions of halides, and oxyanions selected from Groups 3a to 7a and 3b through 7b (see U.S. Pat. No. 4,908,343, issued Mar. 13, 1990).

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist as independent or discrete entities, but are found in combination with charge-balancing counterions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of non-limiting examples, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operation conditions. For example, a catalyst having enhanced selectivity at one set of operating conditions may be operated at a different set of conditions wherein the improvement shows up in the activity rather that the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like.

As used herein, the term "catalytically effective amount of silver" refers to an amount of silver that provides a measurable conversion of ethylene and oxygen to ethylene oxide.

Generally, the carrier is contacted with a silver salt, a silver compound, or a silver complex which has been dissolved in an aqueous solution, so that the carrier is impregnated with said aqueous solution; thereafter the impregnated carrier is separated form the aqueous solution, e.g., by centrifugation or filtration and then dried. The thus obtained impregnated carrier is heated to reduce the silver to metallic silver. It is conveniently heated to a temperature in the range of from about 50° C. to about 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 250° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine solubilizing/reducing agent, and an aqueous solvent.

Suitable silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are particularly useful. The four groups include vicinal alkylenediamines of from 2 to 4 carbon atoms, mixtures of (1) vicinal alkanolamines of from 2 to 4 carbon atoms and (2) vicinal alkylenediamines of from 2 to 4 carbon atoms, mixtures of vicinal alkylenediamines of from 2 to 4 carbon atoms and ammonia, and mixtures of vicinal alkanolamines of from 2 to 4 carbon atoms and ammonia. These solubilizing/reducing agents are generally added in the amount of from about 0.1 to about 10 moles per mole of silver present.

Particularly preferred solubilizing/reducing agents are ethylenediamine, ethylenediamine in combination with ethanolamine, ethylenediamine in combination with ammonia, and ethanolamine in combination with ammonia, with ethylenediamine being most preferred. Ethylenediamine in combination with ethanolamine gives comparable results.

When ethylenediamine is used as the sole solubilizing/reducing agent, it is necessary to add amounts of the amine in the range of from about 0.1 to about 5.0 moles of ethylenediamine per mole of silver.

When ethylenediamine and ethanolamine together are used as the solubilizing/reducing agent, it is suitable to employ from about 0.1 to about 3.0 moles of ethylenediamine per mole of silver and from about 0.1 to about 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein by reference. Methods for preparing silver-containing catalysts with a variety of different promoters are found in U.S. Pat. Nos. 4,908,343, issued Mar. 13, 1990 and 5,057,481, issued Oct. 15, 1991, both incorporated herein by reference.

A particularly preferred process of impregnating the carrier consists of impregnating the carrier with an aqueous solution containing a silver salt of a carboxylic acid, an organic amine and a salt of cesium and a salt of an additional alkali dissolved therein. Silver oxalate is a preferred salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound and a certain amount of an additional alkali metal compound. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water. Rubidium-, potassium-, sodium-, lithium- and mixtures of alkali metal-containing solutions may be prepared also in these ways. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising silver, alkali metal and optional other promoters. As used in the instant specification and claims, the terminology "impregnating the support with one or more solutions comprising silver, alkali metal, and optional other promoters" and similar or cognate terminology means that the support is impregnated in a single or multiple impregnation with one solution containing silver, alkali metal, and optional other promoters in differing amounts; or in multiple impregnations with two or more solutions, wherein each solution contains at least one component selected from silver, alkali metal, and optional other promoter(s), with the proviso that all of the components of silver and alkali metal will individually be found in at least one of the solutions. The concentration of the silver (expressed as the metal) in the silver-containing solution will range from about 1 g/l up to the solubility limit when a single impregnation is utilized. The concentration of the alkali metal (expressed as the metal) will range from about $1 \times 10^{-3}$ g/l up to about 12 g/l and preferably, from about $10 \times 10^{-3}$ g/l to about 12 g/l when a single impregnation step is utilized. Concentrations selected within the above noted ranges will depend upon the pore volume of the catalyst, the final amount desired in the final catalyst and whether the impregnation is single or multiple. Appropriate concentrations can be readily determined by routine experimentation.

It is observed that independent of the form in which the silver is present in the solution before precipitation on the carrier, the term "reduction to metallic silver" is used, while in the meantime often decomposition by heating occurs. We prefer to use the term "reduction", since $Ag^+$ ion is converted into a metallic Ag atom. Reduction times may generally vary from about 0.5 minute to about 8 hours, depending on the circumstances.

The Process

In commercial operation, ethylene and oxygen are converted to ethylene oxide in an ethylene oxide reactor which comprises a large fixed tube heat exchanger containing several thousand tubes filled with catalysts. A coolant is used on the shell side of the reactor to remove the heat of reaction. Coolant temperatures are frequently utilized as an indication of catalyst activity, with high coolant temperatures corresponding to lower catalyst activities.

In the reaction of ethylene oxide with oxygen to produce ethylene oxide, the ethylene is typically present in at least a double amount (on a molar basis) compared with oxygen, but the amount of ethylene employed is generally much higher. The conversion is therefore conveniently calculated according to the mole percentage of oxygen which has been consumed in the reaction to form ethylene oxide and any oxygenated by-products. The oxygen conversion is dependent on the reaction temperature, and the reaction temperature is a measure of the activity of the catalyst employed. The value $T_{40}$ indicates the temperature at 40 percent oxygen conversion in the reactor and the value T is expressed in °C. The temperature for any given catalyst is higher when the conversion of oxygen is higher. Moreover, the temperature is strongly dependent on the employed catalyst and the reaction conditions. The selectivity (to ethylene oxide) indicates the molar amount of ethylene oxide in the reaction product compared with the total molar amount of ethylene converted. In this specification, the selectivity is indicated as $S_{40}$, which means the selectivity at 40 percent oxygen conversion.

The conditions for carrying out such an oxidation reaction in the presence of the silver catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1-2-dichloroethane, vinyl chloride, ethyl chloride or chlorinated polyphenyl compounds, to the desirability of employing recycle operations or applying successive conversions in different reactors to increase the yields of ethylene oxide, and to any other special conditions which may be selected in processes for preparing ethylene oxide. Pressures in the range of from atmospheric to about 500 psig are generally employed. Higher pressures, however, are not excluded. Molecular oxygen employed as reactant can be obtained from conventional sources. The suitable oxygen charge may consist essentially or relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxide reactions is in no way limited to the use of specific conditions among those which are known to be effective. For purposes of illustration only, the following table shows the range of conditions that are often used in current commercial ethylene oxide reactor units and which are also suitable for the instant process.

TABLE I

| *GHSV | 1500–10,000 |
|---|---|
| Inlet Pressure | 150–400 psig |
| Inlet Feed | |
| Ethylene | 1–40% |
| $O_2$ | 3–12% |
| Ethane | 0–3% |
| Chlorohydrocarbon moderator | 0.3–50 ppmv total |
| Argon and/or methane and/or nitrogen diluent | Balance |
| Coolant temperature | 180–315° C. |
| Catalyst temperature | 180–325° C. |
| $O_2$ conversion level | 10–60% |
| EO Production (Work Rate) | 2–25 lbs. EO/cu. ft. catalyst/hr. |

*Cubic feet of gas at standard temperature and pressure passing over one cubic foot of packed catalyst per hour.

In a preferred application of the silver catalysts according to the invention, ethylene oxide is produced when an oxygen-containing gas is contacted with ethylene in the presence of the present catalysts at a temperature in the range of from about 180° C. to about 330° C., and preferably a temperature in the range of from about 200° C. to about 325° C.

While the catalysts of the present invention are preferably used to convert ethylene and oxygen to ethylene oxide, olefins having no allylic hydrogens can be oxidized using the silver catalysts of the present invention to produce a high selectivity of epoxide derivatives thereof by contacting the olefin feed with an oxygen-containing gas in the presence of an organic halide and the silver catalyst described above under defined oxidation conditions.

The process for the selective epoxidation of olefins having no allylic hydrogens comprises contacting the feed olefin, preferably an olefin having at least 4 carbon atoms, with a sufficient quantity of an oxygen-containing gas so as to maintain the molar ratio of olefin to oxygen in the range of about 0.01 up to about 20, in the presence of an organic halide and a silver catalyst at a reaction pressure in the range of about 0.1 up to about 100 atmospheres and a temperature in the range of about 75° up to about 325° C. for a reaction time sufficient to obtain olefin conversions per pass in the range of about 0.1 up to about 75 mole percent.

Olefins contemplated for use in this oxidation process are those which satisfy the following structural formula:

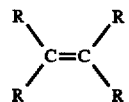

wherein each R is independently selected from the group consisting of:

(a) hydrogen, (b) aryl and substituted aryl groups having in the range of 6 up to 20 carbon atoms, (c) alkyl groups of the formula:

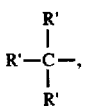

where each R' is independently:

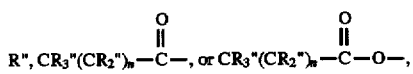

where R" is H, $C_1$-$C_{10}$ alkyl or substituted alkyl, an aryl or substituted aryl group having 6 up to 20 carbon atoms, and n is a whole number from 0-12;

(d) $CR_3"$—$(CR_2")_x$—O—, where x is a whole number from 1-12;

(e)

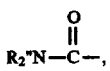

(f) $R_2"N$—;

(g) R"S—;

(h) $CR_2"=CR"-(CR"=CR")_y$, where y is an integer from 0-20; and

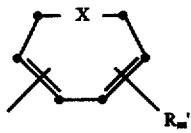

where X is O, S or NR"; and m is an integer from 0-3 with the proviso that said olefin have no allylic hydrogens and that at least one R-group not be hydrogen.

Exemplary olefins which satisfy the above structural formula include butadiene, tertiary butylethylene, vinyl furan, methyl vinyl ketone, N-vinyl pyrrolidone, and the like. A presently preferred olefin for use in the practice of this process is butadiene because of its ready availability, relatively low cost, and the wide range of possible uses for the epoxide reaction product.

The epoxides produced by this process have the structural formula:

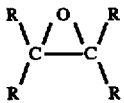

wherein each R is independently defined as set forth above. Where one or more of the R-groups contain carbon-carbon bond unsaturation, further oxidation can be carried out, thereby producing polyepoxide products.

The process is carried out by contacting the olefin to be oxidized with molecular oxygen and an organic halide under oxidation conditions, i.e. in the presence of sufficient quantities of an oxygen-containing gas to provide a molar ratio of olefin to oxygen in the range of about 0.01 up to about 20, and in the presence of about 0.1 up to about 1000 parts per million (by volume of total feed) of organic halide. Preferred quantities of organic halide for use in the practice of the present invention fall within the range of about 1 up to about 100 parts per million, by volume of total feed.

While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures. Similarly, lower levels of organic halide will provide negligible effect on catalyst performance, while higher levels of organic halide would not be expected to provide any significant improvement in catalyst performance.

Suitable oxygen-containing gases include air, oxygen enriched air, substantially purified oxygen, oxygen diluted with inert gases such as $N_2$, Ar, $CO_2$, $CH_4$ and the like.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

Suitable reaction temperatures fall within the range of about 75° C. up to about 325° C. At lower temperatures, the reaction proceeds so slowly as to be impractical, while at higher temperatures undesirable levels of by-products, e.g. carbon dioxide, are obtained. Preferred reaction temperatures fall within the range of about 125° C. up to about 295° C.; with temperatures in the range of about 175° C. up to about 290° C. being most preferred because selectivity to the desired epoxide falls off at temperatures significantly above about 290° C. and space-time yields are undesirably low at temperatures below about 175° C.

The reaction pressure can vary within wide ranges, with typical limits of about 0.1 up to about 100 atmospheres being chosen primarily as a function of safety, handling, equipment, and other practical considerations. Preferably, reaction pressure is maintained in the range of about 1 up to about 30 atmospheres.

Reaction times suitable for this process can vary within wide ranges. Generally, olefin, oxygen, organic halide and catalyst are maintained in contact for a time sufficient to obtain olefin conversions per pass in the range of about 0.1 up to about 75 mole percent. Preferred target olefin conversion levels per pass fall within the range of about 1 up to about 50 mole percent, while reaction times sufficient to obtain olefin conversion per pass in the range of about 5 up to about 30 mole percent are presently most preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the amount of organic halide present in the reaction zone, the reaction temperature and pressure, and the like.

The process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in the range so as to produce the most desirable combination of feed olefin conversion levels and high product selectivity.

Recovery of the epoxide product produced can readily be carried out employing techniques well known by those of skill in the art. For example, where reaction is carried out in the continuous mode, unreacted starting material is initially separated from reaction products; and the desired product is then isolated from the resulting product mixture by distillation, crystallization, extraction, or the like. Since the selectivity to the desired epoxide product is generally quite high, there are only small amounts of undesired reaction products from which to isolate the desired product.

Prior to use for oxidizing olefins having no allylic hydrogens, the silver catalysts (either before or after further treatment with promoter), are optionally calcined in an oxygen-containing atmosphere (air or oxygen-supplemented helium) at about 350° C. for about 4 hours. Following calcination, the silver catalysts are typically subjected to an activation treatment at a temperature in the range of about 300°–350° C. in an atmosphere initially containing about 2–5% hydrogen in an inert carrier such as helium or nitrogen. The hydrogen content of the activating atmosphere is gradually increased up to a final hydrogen concentration of about 20–25% at a controlled rate so that the activation temperature does not exceed 350° C. After the temperature is maintained for about 1 hour at a hydrogen concentration in the range of about 20–25%, catalyst is ready for use.

More detailed descriptions of the silver catalysts and their use in oxidizing olefins having no allylic hydrogens are found in U.S. Pat. No. Nos. 4,897,498, issued Jan. 30, 1990 and 5,081,096, issued Jan. 14, 1992, both of which are incorporated by reference herein.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The invention will be illustrated by the following illustrative embodiments which are provided for illustration only and are not intended to limit the scope of the instant invention.

Illustrative Embodiments

Carrier Preparation

Carriers A, C and E below were prepared according to the invention, i.e., without organic burnout material. Carrier B, D and E below were prepared in a manner similar to Carrier A, except that an organic burnout material was used.

Carrier A

Carrier A was made using the formulations described below, and the procedure used was as follows:

An alpha alumina powder sold in the form of lightly sintered agglomerates was used. These highly agglomerated particles having a volume average particle size of about 60 microns (as measures using a laser light scattering device) were subjected to a milling operation which reduced the agglomerates to the primary particles which had a median particle size of 3.014 3.4 microns, an average crystallite size of 1.8–2.2 microns and a soda content of 0.02–0.06% by weight. These milled particles were then used with agglomerated particles which had not been subjected to any previous milling operation in a 50/50 weight ratio.

The alumina component was used to prepare a formulation of the following ceramic components: 98.8% by weight alpha alumina; 1.0% by weight of zirconia; and 0.2% by weight of magnesium silicate. To this mixture were added 0.1 percent by weight of boric acid, and the components were thereafter mixed for about 45 seconds. Water was then added in an amount necessary to make the mixture extrudable. The mixture was mixed for a further 4 minutes and then 5% by weight of Vaseline™ was added to form an extrudable mixture. The mixture was then mixed for a further 3 minutes before being extruded in the form of hollow cylinders and dried to less than 2% uncombined water. These were then fired in a tunnel kiln with a maximum temperature of about 1385°–1390° C. for about 4 hours. The carrier is described in terms of its physical properties in Table 1.

Carrier B

Carrier B was prepared in a manner similar to Carrier A except that 25% ground walnut shells, i.e., traditional burnout material, was added to the carrier formulation, and only agglomerated particles subjected to a milling operation were used. The carrier is described in terms of its physical properties in Table 1.

Carrier C

Carrier C was made in a manner similar to Carrier A, except that the milled particles had an average crystallite size of 1.6–2.2 microns, and calcium silicate was used in the place of magnesium silicate. The carrier is described in terms of its physical properties in Table 1.

Carrier D

Carrier D was prepared in a manner similar to Carrier B (containing 25% ground walnut shells), except that except that the milled particles had an average crystallite size of 1.6–2.2 microns, and calcium silicate was used in the place of magnesium silicate. The carrier is described in terms of its physical properties in Table 1.

Carrier E

Carrier E was made in a manner similar to Carrier A, except that the highly agglomerated particles having a volume average particle size of about 62 microns, the milled particles had an average crystallite size of 1.0–1.4 microns, the alumina component contained 98.85% by weight alpha alumina and 0.15% calcium silicate was used in the place of magnesium silicate. The carrier is described in terms of its physical properties in Table 1.

Carrier F

Carrier F was prepared in a manner similar to Carrier B (containing 25% ground walnut shells), except that except that the milled particles had an average crystallite size of 1.0–1.4 microns, the alumina component contained 98.7% by weight alpha alumina and 0.3% calcium silicate was used in the place of magnesium silicate. The carrier is described in terms of its physical properties in Table 1.

TABLE 1

CARRIER PROPERTIES

| PROPERTY | Carrier A | Carrier B | Carrier C | Carrier D | Carrier E | Carrier F |
|---|---|---|---|---|---|---|
| Fired Temp. (°C.) | 1390 | 1385 | 1390 | 1390 | 1393 | 1413 |
| Surface Area[1] ($m^2/g$) | 0.99 | 0.77 | 0.92 | 0.51 | 0.99 | 0.66 |
| Pack. Den.[2] ($lb/ft^3$) | 47.8 | 50.8 | 46.1 | 49.8 | 46.1 | 44.0 |
| Water Absorp.[3] (%) | 40.1 | 38.3 | 43.1 | 38.3 | 42.4 | 49.5 |
| Average C.S.[4] (lbs.) | 19.1 | 28.9 | 7.0 | 21.1 | 11.8 | 14.3 |
| Leachable Na[5] (ppm) | 120 | 128 | 71 | 188 | 64 | 48 |
| Leachable K[5] (ppm) | 44 | 103 | 28 | 66 | 32 | 30 |
| Leachable Al[5] (ppm) | 418 | 660 | 558 | 486 | 348 | 510 |
| Leachable Ca[5] (ppm) | 176 | 428 | 700 | 790 | 484 | 1298 |
| Total Leachables[5] | 758 | 1319 | 1357 | 1530 | 928 | 1886 |

[1]"Surface Area" is the BET surface area measured using nitrogen or krypton as the adsorbate.
[2]"Packing Density" is the settled packing density as measured by ASTM D-4699-87, modified by the use of cylinder with an inside diameter of 3¾ inches and a length of 18 inches, or an equivalent.
[3]"Water Absorption" is a measure of the increase in weight of the carrier after being immersed in water and weighed.
[4]"Crush Strength" is measured on a Compton Tensile Tester, model 50-OP.
[5]"Leachables" were measured using the nitric acid solution technique.

Catalyst Preparation

The following illustrative embodiment describes preparative techniques for making the catalysts of the instant invention (Catalysts A, C and E) and the comparative catalysts (Comparative Catalysts B, D and F) and the technique for measuring the properties of these catalysts.

Part A: Preparation of stock silver oxalate/ethylenediamine solution for use in catalyst preparation:

1) Dissolve 415 grams (g) of reagent-grade sodium hydroxide in 2340 milliliters (ml) deionized water. Adjust the temperature to 50° C.

2) Dissolve 1699 g of (high purity) silver nitrate in 2100 ml deionized water. Adjust the temperature to 50° C.

3) Add sodium hydroxide solution slowly to silver nitrate solution with stirring while maintaining a temperature of 50° C. Stir for 15 minutes after addition is complete, and then lower the temperature to 40° C.

4) Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 μmho/cm. Then add back 1500 ml deionized water.

5) Add 630 g of high-purity oxalic acid dihydrate in approximately 100 g increments. Keep the temperature at 40° C. and stir to mix thoroughly. Add the last portion of oxalic acid dihydrate slowly and monitor pH to ensure that pH does not drop below 7.8.

6) Remove as much water from the mixture as possible using clean filter wands in order to form a highly concentrated silver-containing slurry. Cool the silver oxalate slurry to 30° C.

7) Add 699 g of 92 percent weight (%w) ethylenediamine (8% deionized water). Do not allow the temperature to exceed 30° C. during addition.

The above procedure yields a solution containing approximately 27–33% w silver which provides the "stock solution" used in the preparation of Catalysts A, C and E and Comparative Catalysts B, D and F below.

Part B: Preparation of impregnation solutions
For Catalyst A

For preparing impregnated catalyst A, into a 10 milliliter (ml) beaker is added 0.188 grams of $NH_4ReO_4$ dissolved in approximately 2 ml of 50:50 ethylenediamine:$H_2O$, 0.092 grams $Li_2SO_4 \cdot H_2O$ dissolved in 1 gram water, and 0.329 grams $LiNO_3$ dissolved in 2 grams water were added to 180.3 grams of the above-prepared silver solution (specific gravity 1.54 gram/cc), and the resulting solution was diluted with 16.2 grams of water. 0.1572 Grams of stock cesium hydroxide solution containing 46.2% weight cesium was added to 50 grams of the silver oxalate/dopant solution to prepare the impregnation solution.

For Comparative Catalyst B

For preparing impregnated comparative catalyst B, into a 10 ml beaker is added 0.188 grams $NH_4ReO_4$ dissolved in approximately 2 ml of 50:50 ethylenediamine:$H_2O$, 0.079 grams $Li_2SO_4 \cdot H_2O$ dissolved in 1 gram water, and 0.339 grams $LiNO_3$ dissolved in 2 grams water were added to 182.7 grams of the above-prepared silver solution (specific gravity 1.55 grams/cc), and the resulting solution was diluted with 13.3 grams of water. 0.1387 grams of stock cesium hydroxide solution containing 45.5% weight cesium was added to 50 grams of the silver oxalate/dopant solution to prepare the impregnation solution.

For Catalyst C

For preparing impregnated catalyst C, into a 10 ml beaker is added 0.149 grams $NH_4ReO_4$ dissolved in approximately 2 ml of 50:50 ethylenediamine:$H_2O$ 0.073 grams $LiSO_4 \cdot H_2O$ dissolved in 1 gram water, and 0.313 grams $LiNO_3$ dissolved in 2 grams water were added to 168.8 grams of the above-prepared silver solution (specific gravity 1.55 grams/cc), and the resulting solution was diluted with 27.7 grams of water. 0.1424 Grams of stock cesium hydroxide solution containing 46.5% weight cesium was added to 50 grams of the silver oxalate/dopant solution to prepare the impregnation solution.

For Comparative Catalyst D

For preparing impregnated comparative catalyst D, into a 10 ml beaker is added 0.166 grams of $NH_4ReO_4$ dissolved in approximately 2 ml of 50:50 ethylenediamine:$H_2O$, 0.079 grams $Li_2SO_4 \cdot H_2O$ dissolved in 1 gram water, and 0.342 grams $LiNO_3$ dissolved in 2 grams water were added to 181.1 grams of the above-prepared silver solution (specific gravity 1.57 grams/cc), and the resulting solution was diluted with 16.9 grams of water. 0.0939 Grams of stock cesium hydroxide solution containing 46.2% weight cesium was added to 50 grams of the silver oxalate/dopant solution to prepare the impregnation solution.

For Catalyst E

For preparing impregnated catalyst E, into a 10 ml beaker is added 0.201 grams $NH_4ReO_4$ dissolved in approximately 2 ml of 50:50 ethylenediamine:$H_2O$, 0.096 grams $Li_2SO_4 \cdot H_2O$ dissolved in 1 gram water, and 0.103 grams $LiNO_3$ dissolved in 2 grams water were added to 182.3 grams of the above-prepared silver solution (specific gravity 1.56 grams/cc), and the resulting solution was diluted with 13.7 grams of water. 0.1779 Grams of stock cesium hydroxide solution containing 45.8% weight cesium was added to 50 grams of the silver oxalate/dopant solution to prepare the impregnation solution.

For Comparative Catalyst F

For preparing impregnated comparative catalyst F, into a 10 ml beaker is added 0.179 grams $NH_4ReO_4$ dissolved in approximately 2 ml of 50:50 ethylenediamine:$H_2O$, 0.086 grams $Li_2SO_4.H_2O$ dissolved in 1 gram water, and 0.092 grams $LiNO_3$ dissolved in 2 grams water were added to 166 grams of the above-prepared silver solution (specific gravity 1.56 grams/cc), and the resulting solution was diluted with 32 grams of water. 0.1195 Grams of stock cesium hydroxide solution containing 49% weight cesium was added to 50 grams of the silver oxalate/dopant solution to prepare the impregnation solution.

Part C: Catalyst impregnation and curing

Catalyst A

Approximately 30 g of carrier A (described above in Table 1) is placed under 25 mm vacuum for 3 minutes at room temperature. Approximately 50 to 60 g of doped impregnating solution (as described in Part B above under "For Catalyst A") is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. The impregnated carrier is then cured by being continuously shaken in a 300 cu. ft/hr. air stream flowing across a cross-sectional area of approximately 3–5 square inches at 240°–270° C. for 3–6 minutes. The cured catalyst is then ready for testing. The properties of Catalyst A are shown in Table 2 below.

Comparative Catalyst B

Comparative Catalyst B was prepared in the same manner as Catalyst A, except that Catalyst carrier B was used in place of Catalyst carrier A and the impregnating solution used was that described in Part B above under "For Comparative Catalyst B". The properties of Comparative Catalyst B are shown in Table 2 below.

Catalyst C

Catalyst C was prepared in the same manner as Catalyst A, except that Catalyst carrier C was used in place of Catalyst carrier A and the impregnating solution used was that described in Part B above under "For Catalyst C". The properties of Catalyst C are shown in Table 2 below.

Comparative Catalyst D

Comparative Catalyst D was prepared in the same manner as Catalyst A, except that Catalyst carrier D was used in place of Catalyst carrier A and the impregnating solution used was that described in Part B above under "For Comparative Catalyst D". The properties of Comparative Catalyst D are shown in Table 2 below.

Catalyst E

Catalyst E was prepared in the same manner as Catalyst A, except that Catalyst carrier E was used in place of Catalyst carrier A and the impregnating solution used was that described in Part B above under "For Catalyst E". The properties of Catalyst E are shown in Table 2 below.

Comparative Catalyst F

Comparative Catalyst F was prepared in the same manner as Catalyst A, except that Catalyst carrier F was used in place of Catalyst carrier A and the impregnating solution used was that described in Part B above under "For Comparative Catalyst F". The properties of Comparative Catalyst F are shown in Table 2 below.

TABLE 2

CATALYST PROPERTIES

| | Ag (wt %) | Cs (ppm) | $Li_2SO_4$ (μmol/g) | $LiNO_3$ (μmol/g) | Re (μmol/g) |
|---|---|---|---|---|---|
| Catalyst A | 13.2 | 738 | 1.8 | 12.0 | 1.8 |
| Comp. Cat. B | 13.2 | 645 | 1.5 | 12.0 | 1.5 |
| Catalyst C | 13.2 | 727 | 1.5 | 12.0 | 1.5 |
| Comp. Cat. D | 13.2 | 444 | 1.5 | 12.0 | 1.5 |
| Catalyst E | 14.5 | 828 | 2 | 4.0 | 2.0 |
| Comp. Cat. F | 14.5 | 599 | 2 | 4.0 | 2.0 |

The actual silver content of the catalyst can be determined by any of a number of standard, published procedures. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/ Procedure

A. For Catalysts A and Comparative Catalysts B 3 to 5 Grams of crushed catalyst (14–20 mesh) are loaded into a 0.21 inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 3300. The outlet gas pressure is 210 psig.

The gas mixture passed thorough the catalyst bed (in once-through operation) during the entire test run (including startup) consists of 30% ethylene, 8.5% oxygen, 5% carbon dioxide, 54.5% nitrogen, and 0.5 to 6 ppmv ethyl chloride with the balance being nitrogen/argon.

The startup procedure involved ramping the temperature from 225° C. to 245° C. in the following fashion: 1 hour at 225° C., 1 hour at 235° C., and 1 hour at 245° C., and then the temperature was adjusted so as to achieve a constant oxygen conversion level of ($T_{40}$). The moderator level is varied and run for 4–24 hours at each level to determine maximum selectivity. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performance of catalysts tested at different times, all catalysts described in this illustrative embodiment were tested simultaneously with a standard reference catalyst which was $S_{40}$=81.0% and $T_{40}$=230° C.

Catalysts A and Comparative Catalyst B prepared above were tested using the above procedure, measurements were taken continuously and are reported in Table 3 below at 150 days, 200 days and 250 days to provide an indication of the selectivity stability of the catalysts over time. All selectivity values are expressed as % and all activity values are expressed as °C.

TABLE 3

CATALYST PERFORMANCE OVER TIME

| | $S_{40}$, % | | | $T_{40}$, °C. | | |
|---|---|---|---|---|---|---|
| | 150 Days | 200 Days | 250 Days | 150 Days | 200 Days | 250 Days |
| Catalyst A | 84.8 | 83.8 | 83.0 | 269 | 277 | 279 |
| Comparative Catalyst B | 84.8 | 82.6 | 81.5 | 277 | 281 | 284 |

B. For Catalyst C and Comparative Catalyst D

Catalyst C and Comparative Catalyst D were tested in a manner similar to Catalyst A and Comparative Catalyst B above, except that an accelerated aging test as set forth hereinafter was utilized. After the initial performance values for selectivity and activity at 40% oxygen conversion were obtained as above, the catalysts were brought to 85% oxygen conversion or to a maximum temperature of 285° C. to a ten day period to accelerate the aging of the catalyst. After this ten day aging period, the oxygen conversion is reduced to 40% and the performance is re-optimized using the ethyl chloride moderator under standard conditions. This cycle is then repeated so that the selectivity and activity decline of the catalyst is measured under the standard 40% oxygen conversion conditions after each ten day period at 85% oxygen conversion or a maximum temperature of 285° C. Table 4 shows the performance at 40% oxygen conversion aging for the number of days indicated at 85% oxygen conversion or a maximum temperature of 285° C.

TABLE 4

CATALYST PERFORMANCE OVER TIME

| | $S_{40}$, % Days | | | | $T_{40}$, °C. Days | | | |
|---|---|---|---|---|---|---|---|---|
| | 20 | 40 | 60 | 80 | 20 | 40 | 60 | 80 |
| Catalyst C | 86.7 | 85.9 | 83.7 | 83 | 260 | 268 | 275 | 280 |
| Comparative Catalyst D | 83.8 | 82.4 | 80.5 | 77.8 | 259 | 265 | 267 | 275 |

C. For Catalyst E and Comparative Catalyst F

Catalyst E and Comparative Catalyst F were tested in a manner similar to Catalyst A and Comparative Catalyst B above, except that a higher severity accelerated aging test as set forth hereinafter was utilized. 0.7–0.8 Grams of crushed catalyst (40–80 mesh) were loaded into a 3.8 millimeter (inside diameter) stainless steel U-shaped tube. The weight of the catalyst used and the inlet gas flow rate are adjusted to achieve a gas hourly space velocity of 16,500 ccs of gas per cc of catalyst per hour. The outlet gas pressure is 210 psig. Prior to being contacted with the reactant gases, the catalysts were treated with nitrogen gas at 225° C. for twenty-four hours. The gas mixture passed thorough the catalyst bed (in once-through operation) during the entire test run (including startup) consists of 30% ethylene, 8.5% oxygen, 7% carbon dioxide, 54.5% nitrogen, and with 4 ppmv ethyl chloride and 4 ppmv vinyl chloride as moderators. The startup procedure involved ramping the temperature from 225° C. to 245° C. in the following fashion: 1 hour at 225° C., 1 hour at 235° C., and 1 hour at 245° C., and then the temperature was adjusted so as to achieve a constant oxygen conversion level of ($T_{40}$). The selectivity and activity loss relative to the initial performance as a function of days on stream are given in Table 5 below.

TABLE 5

CATALYST SELECTIVITY AND ACTIVITY LOSS OVER TIME

| | $S_{40}$, % Days | | | | $T_{40}$, °C. Days | | | |
|---|---|---|---|---|---|---|---|---|
| | 10 | 20 | 30 | 40 | 10 | 20 | 30 | 40 |
| Catalyst E | 2.2 | 2.2 | 3.5 | 5.2 | 18 | 21 | 31 | 34 |
| Comparative Catalyst F | 1.8 | 3.5 | 8.5 | 9.0 | 15 | 25 | 38 | 41 |

As can be seen in the above examples and specifically in Tables 3, 4, and 5, the catalysts which were prepared without organic burnout materials, i.e., Catalysts A, C and E, have improved selectivity stabilities over catalysts which were prepared using organic burnout materials, i.e., Comparative Catalysts B, D and F.

What is claimed is:

1. A catalyst suitable for the vapor phase production of ethylene oxide from ethylene and oxygen comprising a catalytically effective amount of silver and a promoting amount of alkali metal(s) deposited on a carrier prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier.

2. The catalyst of claim 1 wherein, in the carrier, the ceramic components of the mixture comprise at least about 85 percent by weight of alpha alumina, from about 0.01 percent by weight to about 6.0 percent by weight of an alkaline earth metal silicate selected from the group consisting of calcium and magnesium silicates and from about 0.01 percent by weight to about 10 percent by weight of zirconia.

3. The catalyst of claim 1 wherein, in the carrier, the alpha alumina component has a bimodal particle size distribution with a first mode having an average particle size of from about 15 microns to about 120 microns and a second mode having an average particle size that is less than one-half that of the first mode and is between about 1 and about 15 microns.

4. The catalyst of claim 1 wherein, in the carrier, the alpha alumina component selected comprises lightly sintered agglomerates with a median particle size of from about 15 microns to about 120 microns.

5. The catalyst of claim 4 wherein, in the carrier, the alpha alumina component selected comprises lightly sintered agglomerates with a median particle size of from about 30 microns to about 90 microns.

6. The catalyst of claim 1 wherein, in the carrier, the ceramic components further comprise a compound that forms titania when the carrier is fired in an amount sufficient to provide the equivalent of from about 0.01 percent by weight to about 5 percent by weight of titania.

7. The catalyst of claim 1 wherein the silver ranges from about 1 percent by weight to about 40 percent by weight of the total catalyst and the alkali metal ranges from about 10 parts per million to about 3000 parts per million, expressed as the metal, by weight of the total catalyst.

8. The catalyst of claim 7 wherein said alkali metal promoter is selected from the group consisting of potassium, rubidium, cesium, lithium and mixtures thereof.

9. The catalyst of claim 8 wherein said promoter is cesium.

10. The catalyst of claim 1 wherein said alkali metal promoter comprises cesium plus at least one additional alkali metal.

11. The catalyst of claim 1 wherein the catalyst additionally comprises a promoting amount of rhenium.

12. The catalyst of claim 11 wherein the catalyst additionally comprises a rhenium co-promoter selected from the group consisting of sulfur, molybdenum, tungsten, chromium, phosphorus, boron and mixtures thereof.

13. A catalyst suitable for the vapor phase production of ethylene oxide from ethylene and oxygen comprising a catalytically effective amount of silver and a promoting amount of alkali metal deposited on a carrier prepared by a process which comprises:
  a) providing a mixture consisting essentially of:
    i) ceramic components comprising at least about 90 percent by weight of alpha alumina, from about 0.01 percent by weight to about 10.0 percent by weight (measured as the oxide, MO) of an alkaline earth metal oxide, from about 0.01 percent by weight to about 10.0 percent by weight (measured as the silica) of a silicon oxide, and from about zero to about 15 percent by weight (measured as the dioxide) of zirconium in the form of an oxide;
    ii) a liquid carrier medium in an amount to render the mixture shapable; and
    iii) a total amount of from zero to about 15 percent by weight of ceramic bond, lubricant and/or forming aids;
  b) shaping the mixture to form a carrier precursor;
  c) drying the carrier precursor to remove the liquid from the carrier medium; and
  d) firing the precursor to form a carrier with a porosity of from about 15 percent to about 60 percent,
wherein the particle sizes of the ceramic components are chosen such that the packing density of the dried precursor is not greater than that of the fired carrier.

14. The catalyst of claim 13 wherein, in the carrier, the ceramic components of the mixture comprise at least about 85 percent by weight of alpha alumina, from about 0.01 percent by weight to about 6.0 percent by weight of an alkaline earth metal silicate selected from the group consisting of calcium and magnesium silicates and from about 0.01 percent by weight to about 10 percent by weight of zirconia.

15. The catalyst of claim 13 wherein, in the carrier, the alpha alumina component has a bimodal particle size distribution with a first mode having an average particle size of from about 15 microns to about 120 microns and a second mode having an average particle size that is less than one-half that of the first mode and is between about 1 and about 15 microns.

16. The catalyst of claim 13 wherein, in the carrier, the alpha alumina component selected comprises lightly sintered agglomerates with a median particle size of from about 15 microns to about 120 microns.

17. The catalyst of claim 16 wherein, in the carrier, the alpha alumina component selected comprises lightly sintered agglomerates with a median particle size of from about 30 microns to about 90 microns.

18. The catalyst of claim 13 wherein, in the carrier, the ceramic components further comprise a compound that forms titania when the carrier is fired in an amount sufficient to provide the equivalent of from about 0.01 percent by weight to about 5 percent by weight of titania.

19. The catalyst of claim 13 wherein the silver ranges from about 1 percent by weight to about 40 percent by weight of the total catalyst and the alkali metal ranges from about 10 parts per million to about 3000 parts per million, expressed as the metal, by weight of the total catalyst.

20. The catalyst of claim 19 wherein said alkali metal promoter is selected from the group consisting of potassium, rubidium, cesium, lithium and mixtures thereof.

21. The catalyst of claim 20 wherein said promoter is cesium.

22. The catalyst of claim 13 wherein said alkali metal promoter comprises cesium plus at least one additional alkali metal.

23. The catalyst of claim 13 wherein the catalyst additionally comprises a promoting amount of rhenium.

24. The catalyst of claim 23 wherein the catalyst additionally comprises a rhenium co-promoter selected from the group consisting of sulfur, molybdenum, tungsten, chromium, phosphorus, boron and mixtures thereof.

25. A process for the production of ethylene oxide wherein ethylene is contacted in the vapor phase with an oxygen-containing gas at ethylene oxide forming conditions at a temperature in the range of from about 180° C. to about 330° C. in the presence of a catalyst comprising a catalytically effective amount of silver and a promoting amount of alkali metal deposited on a carrier prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier.

26. A process for the epoxidation of olefins having no allylic hydrogens wherein an olefin having no allylic hydrogen is contacted in the vapor phase with an oxygen-containing gas at epoxide forming conditions at a temperature in the range of from about 75° C. to about 325° C. in the presence of an organic halide and a catalyst comprising a catalytically effective amount of silver and a promoting amount of alkali metal deposited on a carrier prepared by a process which comprises: a) providing a mixture consisting essentially of: i) ceramic components comprising at least about 80 percent by weight of alpha alumina, from about 0.01 percent by weight to about 10 percent by weight (measured as the oxide, MO) of an alkaline earth metal oxide, from about 0.01 percent by weight to about 10 percent by weight (measured as the silica) of a silicon oxide, and from about zero to about 15 percent by weight (measured as the dioxide) of zirconium in the form of an oxide; ii) a liquid carrier medium in an amount to render the mixture shapable; and iii) a total amount of from zero to about 15 percent by weight of ceramic bond, lubricant and/or forming aids; b) shaping the mixture to form a carrier precursor; c) drying the carrier precursor to remove the liquid from the carrier medium; and d) firing the precursor to form a carrier with a porosity of from about 15 percent to about 60 percent, wherein the particle sizes of the ceramic components are chosen such that the packing density of the dried precursor is not greater than that of the fired carrier.

* * * * *